(12) United States Patent
Hardy et al.

(10) Patent No.: US 10,632,224 B2
(45) Date of Patent: Apr. 28, 2020

(54) WOUND CARE DEVICE

(75) Inventors: Craig Hardy, Cheshire (GB); Stewart Andrew Darby, Stroke on Trent (GB)

(73) Assignee: Medtrade Products Limited, Cheshire (GB)

( * ) Notice: Subject to any disclaimer, the term of this patent is extended or adjusted under 35 U.S.C. 154(b) by 0 days.

(21) Appl. No.: 13/063,891

(22) PCT Filed: Sep. 14, 2009

(86) PCT No.: PCT/GB2009/002184
§ 371 (c)(1),
(2), (4) Date: May 27, 2011

(87) PCT Pub. No.: WO2010/031995
PCT Pub. Date: Mar. 25, 2010

(65) Prior Publication Data
US 2011/0236433 A1    Sep. 29, 2011

(30) Foreign Application Priority Data
Sep. 17, 2008   (GB) .................................. 0817014.4

(51) Int. Cl.
| | | |
|---|---|---|
| A61K 9/00 | (2006.01) | |
| A61K 33/38 | (2006.01) | |
| A61P 17/02 | (2006.01) | |
| A61P 31/00 | (2006.01) | |
| A61P 7/04 | (2006.01) | |
| A61K 31/722 | (2006.01) | |
| A61L 15/60 | (2006.01) | |
| C08L 1/00 | (2006.01) | |
| C08L 5/00 | (2006.01) | |

(52) U.S. Cl.
CPC ................ *A61L 15/60* (2013.01); *C08L 1/00* (2013.01); *C08L 5/00* (2013.01)

(58) Field of Classification Search
None
See application file for complete search history.

(56) References Cited

U.S. PATENT DOCUMENTS

| | | | | |
|---|---|---|---|---|
| 3,122,479 A * | 2/1964 | Smith | ........................... | 222/192 |
| 3,915,959 A * | 10/1975 | Goheen et al. | ............... | 536/101 |
| 5,134,229 A * | 7/1992 | Saferstein et al. | .............. | 536/56 |
| 6,268,544 B1 * | 7/2001 | Court | ................ | A61F 13/00008 |
| | | | | 602/41 |
| 6,844,430 B2 * | 1/2005 | Pesce et al. | .................... | 536/20 |
| 6,998,509 B1 * | 2/2006 | Nielsen | ................... | A61L 15/28 |
| | | | | 602/48 |
| 2006/0149182 A1 * | 7/2006 | Cullen et al. | .................... | 602/49 |
| 2006/0172000 A1 * | 8/2006 | Cullen et al. | ................. | 424/445 |

FOREIGN PATENT DOCUMENTS

| | | |
|---|---|---|
| EP | 1882482 A2 | 1/2008 |
| WO | WO 0124840 A1 * | 4/2001 |
| WO | WO 02102276 A2 * | 12/2002 |
| WO | 03092755 A1 | 11/2003 |

\* cited by examiner

*Primary Examiner* — Dominic Lazaro
(74) *Attorney, Agent, or Firm* — Barlow, Josephs & Holmes, Ltd.

(57) ABSTRACT

An absorbent wound care device includes two or more materials which individually do not gel when exposed to a fluid but do gel when brought together and exposed to a fluid. The device is particularly intended for haemostatic use and for absorbing bodily fluids being emitted from wounds and physiological target sites.

7 Claims, No Drawings

WOUND CARE DEVICE

The present invention relates to a wound care device, and more specifically to an absorbent wound care device comprising two or more materials which individually do not gel when exposed to a fluid but do gel when brought together and exposed to a fluid.

There are many circumstances in which animals, both human and non-human, may become injured or wounded causing discharge of bodily fluids. When treating wounds which are exuding blood and other bodily fluids, it is advantageous to have an absorbent dressing which is capable of adapting to the conformation of any individual wound. Such dressings may be obtained by using fibre dressings or hydrogels. Fibrous wound dressings often present problems in terms of insufficient absorption of the bodily fluids, and/or they may suffer from a lack of cohesion, which may result in the dressing not being able to be removed from a wound in one piece.

Gel-based dressings have the benefit of being cohesive so that they do not stick to a wound site, making it possible to remove the dressing from the wound in one piece while providing an ideal moisture environment for wound healing. Additionally, they can have a low adherence to a wound site, allowing them to be removed from a wound easily without causing pain for the wounded party.

Wound care devices such as absorbent dressings comprising fibres which can gel are known in the art. U.S. Pat. No. 6,998,509 describes a wound care device which comprises chitosan fibres, which are capable of absorbing liquid to form a swollen coherent gel. The chitosan fibres are normally insoluble, non-swelling and non-gelling and so are treated with an acid and heat to convert them into an insoluble, water-swelling and water-gelling form. A similar wound care device is also detailed in US 2005/0058694. Such dressings employing the use of gels effectively serve to entrap the absorbed fluids.

There are also antibacterial wound dressings based on gel-forming fibres such as carboxymethyl cellulose. Such dressings are described in, for example, EP1882482 and WO03092755. However, the carboxymethyl cellulose fibres are able to gel on their own.

It is an object of the present invention to provide a wound care device which exhibits good gel-forming properties upon contact with a fluid and which is cost effective, and also to provide a process which involves minimal use of potentially dangerous materials and which exhibits minimal environmental impact.

In accordance with the invention, there is provided a wound care device comprising a first material and a second material, which first and second materials individually do not substantially gel when exposed to a fluid but do gel when brought together and exposed to a fluid.

Typically, the first and second materials are different. Individually, the first material and the second material substantially do not gel at all when exposed to a fluid. It is only when they are brought together and combined in the wound care device of the invention and are in the presence of a fluid, such as water, saline, wound exudates or blood, i.e. fluids that the wound care device would usually come into contact with when being used on a physiological target site, that any gelling occurs.

The physiological target site may be any site in or on the body of an animal. The animal may be a human or a non-human animal. The physiological target site may be a wound or it may be an opening in a body caused during a medical procedure, for example during surgery. Hereinafter, the physiological target site is referred to as a wound for illustrative purposes only.

Typically, there are only two materials comprising the device, but there may be more materials if desired, such as three, four, five, or six different materials. Non-limiting examples of materials which could be used include materials to speed up or slow down the availability of the acid, or any materials which would not effect the gelling but would add wet/dry strength, such as another already complete nonwoven fabric, a polymer net, a knitted fabric or strong fibres or adhesive/cohesive agents to hold the fabric together.

Further components which could be added include but are not limited to wetting agents such as surfactants, colouring agents, adhesives to give the fabric a sticky texture, processing aids, inert materials, bulking agents, absorbent polymers, antimicrobials and meltable agents to help the fabric stick together.

According to one aspect of the invention, the two materials may be mixed together in the device or may be segregated in separate layers or sections of the device. The resulting gelling pad could be used as a component in a wound dressing construction, for example, as the absorbent part of a more complicated structure with alternative backing, adhesive or wound contact materials.

According to one embodiment of the invention, the backing may comprise medical grade sheet materials such as but not limited to polymer films, thin foams and fabrics e.g polyurethane films, polyurethane foams, nonwoven fabrics, etc.

According to another embodiment, suitable skin contact adhesives may include, but are not limited to, acrylate, silicone, or polyurethane based adhesives. They can be based on hydrogels and can be porous to moisture with a high moisture vapour transmission rate. They can be applied from water emulsions, solvents or using hot melt systems. The adhesives should have a good skin tack but give minimal skin trauma on removal. They can constitute 100% coverage of the backing, or a partial coverage thereof in the form of a pattern or mesh.

According to another embodiment, the wound contact materials can include, but are not limited to, non-adherent layers which give very low or no adhesion to skin, wicking layers to speed up the absorption of fluid, active carrier layers for delivery of a therapeutic material (such as a pharmaceutical, haemostat, antimicrobial, wound healing agent, or scar reducing agent) and adhesive layers to help in holding the dressing in place while potentially reducing trauma on removal. They can be based on a polymer mesh, a fabric (e.g. nonwoven), and a hydrogel adhesive or partial adhesive coverings.

According to another aspect, one or more of the materials may be fibrous, and the first and second materials may comprise a fibrous wound dressing.

The first material typically comprises an absorbent polymer such as chitosan or a partially de-acetylated chitin, and will not substantially gel on its own when exposed to fluids. Any non-gelling chitosan or chitin salt or any blend of chitosan and/or chitin and their salts may be used so long as the combination of substances used for the first material does not substantially gel when exposed to fluids. An amount of a soluble (still non-gelling) chitosan salt could be advantageous so long as the combination does not gel when exposed to fluids.

Chitosan is a derivative of solid waste from shell fish processing and can be extracted from fungus culture. It is a water insoluble cationic polymeric material.

The chitosan salt is prepared in situ when the acid comes into contact with the chitosan with an appropriate acid. It will be appreciated that the acid may be any inorganic or organic acid which yields a chitosan salt. Suitable acids would be recognised by a skilled person.

Typically, the molecular weight of the chitosan used for the preparation of the wound care device according to the present invention is less than about 2,000,000, more typically less than about 1,000,000, and even more typically less than about 500,000, and most typically less than about 175,000.

Chitosan fibres suitable for use as the first material in accordance with the invention are typically fibres with a deacetylation degree above about 50%, more typically above about 75% and most typically above about 85%.

Typically, the fibres have a minimum average length of about 3 mm and a maximum length of about 150 mm, more typically no more than about 76 mm. The preferred proportion between length and diameter of the fibres is at least 25; more preferred at least 80 and most preferred at least 500.

The fibrous structure of the chitosan according to the present invention may provide an essential coherence for use in a wound dressing. When used as e.g. a wound contacting fabric, it is important that the absorbent material is coherent, thus rendering it possible to remove the wound dressing in one piece from the wound.

The second material may be any non-gelling material. Such a material should be able to absorb or act as a carrier for an acid without permanent bonding occurring. Typical materials include but are not limited to polymers such, as cellulose, cellulose derivatives (e.g. ethyl cellulose, methyl cellulose, etc), cotton, alginate viscose, polypropylene, polyethylene or any combination of such materials.

According to one embodiment, the second material typically has one or more acids associated therewith, which are typically absorbed therein. The acid is generally an organic acid, although inorganic acids may also be used. Examples of acids which could be used in accordance with the invention include, but are not limited to, formic, acetic, halogen acetic acids (such as fluoro- or chloroacetic acids), ascorbic, hydrochloric, sulphuric, propanoic, propenoic, lactic, succinic, acrylic, glyoxylic, pyruvic or a hydroxy propionic/butanoic acid. The second material will not substantially gel on its own when exposed to fluids. More typically, the acids used are one or more acids selected from lactic, acetic and succinic acids. Most typically, the acid used comprises lactic and/or acetic acids. The use of an acid which is already present in the body could be an advantage in some potential indications.

When the first and second materials are brought together in the form of a wound care device and the device is placed on to a surface of a body which has fluids associated therewith (typically a wound site on a human or animal body), the fluid causes the acid contained within the second material to be released. The acid then comes into contact with the first material containing the chitosan or partially de-acetylated chitin. The acid reacts with the chitosan or partially de-acetylated chitin to form the corresponding salt. The acid is typically at least partially soluble in the fluid to aid transmission.

The contact with the acid converts the first material containing the chitosan or partially de-acetylated chitin from a non-swelling, non-gelling material to a swellable, gellable material, but one which is still substantially water insoluble. Once the converted first material comes into contact with the fluid from the wound site it gels in situ, effectively encapsulating the fluid.

The first and second materials are typically combined together to make a nonwoven fabric, and are typically carded or needled together.

Although the chitosan is typically insoluble, it is also possible for the chitosan to be at least partially or completely dissolved in the presence of the acid, if desired. If a soluble chitosan salt is required, the acid used to react with the chitosan must be one which yields a salt which is soluble in bodily fluids. The appropriate acids or combination of acids for yielding a soluble chitosan salt will be apparent to a skilled person. For example, chitosan phosphate is substantially insoluble in water, and so use of phosphoric acid alone would hence be less suitable as the acid for this purpose. Therefore, a portion of the chitosan for use with the present invention can be first converted into a water soluble salt so that it is soluble in blood and can act as a haemostat to form a gel/clot with the blood to stem blood flow.

Chitosan can act as a haemostat in two ways; either by gelling with water in the blood and bonding to wet tissue to plug a wound, or by dissolving and bonding with the surface of red blood cells to create a clot-like gel. The properties of the combinations of chitosan and acid are dependent upon the nature of the chitosan (e.g. molecular weight and degree of deacetylation), as well as the particular acid used and the quantities present.

The presence of the acid in the second material removes the need to pre-treat the chitosan-containing first material with an acid. Carboxymethyl cellulose fibre used in existing wound care devices requires the treatment of cellulose fibre with toxic acids in a volatile solvent.

The wound care device of the invention removes the need for using volatile solvents, reduced pollution and risk of exposure to hazardous materials for workers, as well as providing a less expensive and easier process to carry out. The waste materials which are produced are cheaper to process and are more environmentally friendly. Additionally, some actives are easy to apply in a water base, so new and different materials can be easily incorporated.

Furthermore, all the fibres in wound care device of the invention will not individually gel if they are kept separate from each other.

According to another embodiment of the invention, the wound care device may include one or more wound healing agents, one or more antimicrobial agents, such as silver, silver salts, silver-containing compounds, fibres containing silver, chlorhexidine, etc; growth factors; cytokines; agents which absorb agents which delay healing such as MMP's (matrix metalloproteinases) and elastase, and/or haemostats. The active agent could be presented on either of the first or second fibres, or on a third material.

According to another embodiment, surfactants could be used to help the wetting out of the dressing, and or inert materials could be included either to help the wetting out, or to add strength or bulk. Typical levels of any of these components could be from ppm levels up to about 50%. More typical levels would be less than about 10%, still more typically less than about 5%.

According to another embodiment of the invention, the wound care device may be used as part of a haemostatic material, and could comprise one or more further haemostats other than chitosan, such as a polysaccharide or a mineral such as clay or kaolin. By "haemostat", it is meant any agent which is capable of producing a clot or plug which stops or reduces bleeding when it comes into contact with blood.

In this embodiment, the chitosan is at least partially dissolved by the acid from the second material and/or the fluid from the physiological target site and is absorbed into the body. The presence of the haemostat in the bodily fluid causes the e.g. blood to clot more quickly and stems the blood flow.

Chitosan salts are ideally suited for the applications described herein as chitosan is readily broken down in the body. Chitosan is converted to glucosamine by the enzyme lysozyme and is therefore excreted from the body naturally. It is not necessary to take any measures to remove the chitosan from the body; however, it can be removed if desired.

Furthermore, chitosan salts exhibit mild antibacterial properties and as such their use reduces the risk of infection.

The viscosity of the chitosan used according to the invention may typically be less than about 1000 cP, more typically less than about 500, even more typically less than about 300. Advantageously, the viscosity is from about 40 to about 200 cps.

According to another embodiment of the invention, other haemostats which could be used include but are not limited to calcium, vitamin K, fibrinogen, thrombin, factor VII, factor VIII, clays such as kaolin, oxidised regenerated cellulose, gelatin, or collagen, etc.

By the terms "water-swelling", "water-gelling" and "substantially water-insoluble" is meant that when the fibres are contacted with a fluid, such as water, saline, wound exudates or blood, they will absorb the fluid and swell by forming a gel, and will not substantially dissolve.

The wound care device of the invention may take any suitable form and may be provided in a range of different sizes, shapes and thicknesses necessary to deal with a wound, such as square, rectangular, circular or elliptical. For example, the device may be a generally flat shape with little height relative to its width/depth. Any regular or irregular shape may be employed. It may be provided in large sheets which can be cut to the required size.

The thickness of the device may be varied between upper and lower limits as desired. The upper limit of the thickness is typically about 5 cm, down to a few microns, such as 5-10 microns. It is however important that the device is flexible so that it can be curved to fit the contours of the body.

The chitosan typically has a pH of from about 6.0 to about 8.0. Chitosan salts can have a pH from about 3.5 to about 8.0. The pH is largely dependent upon the particular chitosan or chitosan salt used, as they each have a different pH.

The chitosan material may be provided in a sterile or non-sterile form. Where the material is provided in a non-sterile form, sterilisation may be carried out using any of the known methods, such as gamma irradiation, electron beam treatment, heat treatment, etc. A material in a non-sterile form may be provided in combination with one or more preservatives.

According to a further aspect of the invention, there is provided a method of manufacturing a wound care device comprising a first material and a second material, which materials individually do not substantially gel when exposed to a fluid but do gel when brought together and exposed to a fluid, comprising the steps of:
i) providing a first material and second material, which materials individually do not substantially gel when exposed to a fluid but do gel when brought together and exposed to a fluid; and
ii) bringing the first material and second material together.

The present invention also provides a method of absorbing a discharge of a fluid from a physiological target site, such as a wound area. There is also provided a method of absorbing a discharge of a fluid from a physiological target site comprising the steps of cleaning the target site where necessary, applying to the target site a wound care device as described herein and applying pressure to the site until a gel forms.

According to a further aspect of the invention, there is provided a use of a wound care device as described herein in absorbing a discharge of a bodily fluid from a physiological target site.

The invention will now be described further by way of example with reference to the following examples which are intended to be illustrative only and in no way limiting upon the scope of the invention.

EXAMPLES

Test Method

The dry sample is weighed and recorded as W1. The sample is then wet with an excess of the test fluid. After 10 minutes the sample is held by a corner and allowed to drain for 1 minute.

It is then weighed to give W2.

An assessment is made of the gelling of the sample. This is recorded as either;
1) no or minimal gelling
2) some gelling
3) good gel
4) partially dissolving
5) substantially soluble An assessment is made of the wet integrity of the sample. This is recorded as either:
1) Integral
2) Low Integrity
3) Very low Integrity Absorbency in g/g is calculated as (W2−W1)/W1.

Single Component Samples

Sample 1

2.4 dtex cellulose staple fibres (Lenzing, Austria) were carded and needled to make a nonwoven fabric.

Sample 2

Acetic acid was added to Sample 1 above to give a concentration of 20% w/w. The resulting fibres were carded and needled to a nonwoven fabric.

Sample 3

Acetic acid was added to Sample 1 above to give a concentration of 30% w/w. The resulting fibres were carded and needled to a nonwoven fabric.

Sample 4

Lactic acid was added to Sample 1 above to give a concentration of 10% w/w. The resulting fibres were carded and needled to a nonwoven fabric.

Sample 5

Acetic acid was added to Sample 1 above to give a concentration of 10% w/w. Lactic acid was added to give an additional concentration of 10% w/w. The resulting fibres were carded and needled to a nonwoven fabric.

Sample 6

1.7 dtex chitosan staple fibres were carded and needled to make a nonwoven fabric Sample 7

2.4 dtex chitosan staple fibres were carded and needled to make a nonwoven fabric Sample 8

10% w/w acetic acid and 10% w/w succinic acid were added to 1.7 dtex chitosan staple fibres in an excess of ethanol which were then dried at 30° C. The resulting fibres were carded and needled to make a nonwoven fabric.

Sample 9
1.7 dtex Chitosan staple fibres were hand carded to produce an open absorbent web matt of fibres.
Sample 10
2.4 dtex cellulose staple fibres were hand carded to produce an open absorbent web matt of fibres.
Sample 11
Sorbsan, (Uno Medical, UK), alginate fibres in carded web/fabric.
Sample 12
2.4 dtex cotton staple fibres were handed carded to produce a carded and needled nonwoven fabric.
Sample 13
Viscose/polypropylene thermal bonded fabric (Lantor, UK).
Sample 14
0.5% silver nitrate was added to 2.4 dtex chitosan staple fibres in an excess of water which were then dried at 60° C. The resulting fibres were carded and needled to make a nonwoven fabric.
Sample 15
2% tween 20 was added to 2.4 dtex chitosan staple fibres in an excess of water which were then dried at 60° C. The resulting fibres were carded and needled to make a nonwoven fabric.
Sample 16
1% calcium lactate was added to 2.4 dtex chitosan staple fibres in an excess of water which were then dried at 60° C. The resulting fibres were carded and needled to make a nonwoven fabric.
Sample 17
The same 2.4 dtex cellulose staple fibre used in sample 1 was blended 50/50 with the same chitosan fibres used in Sample 6. No acid was added. The combined fibres were carded and needled to make a nonwoven fabric.

| Sample | Gelling | Wet Integrity | Comments |
| --- | --- | --- | --- |
| 1 | None | Integral | Fibres within sample are not swollen or gelled |
| 2 | None | Integral | Fibres within sample are not swollen or gelled |
| 3 | None | Integral | Fibres within sample are not swollen or gelled |
| 4 | None | Integral | Fibres within sample are not swollen or gelled |
| 5 | None | Integral | Fibres within sample are not swollen or gelled |
| 6 | None | Integral | Fibres within sample are not swollen or gelled |
| 7 | None | Integral | Fibres within sample are not swollen or gelled |
| 8 | None | Integral | Fibres within sample are not swollen or gelled |
| 9 | None | Integral | Fibres within sample are not swollen or gelled |
| 10 | None | Integral | Fibres within sample are not swollen or gelled |
| 11 | Some gelling | Low Integrity | Fibres within sample show some gelling/swelling. There is still substantial saline held between the fibres rather than within them. |
| 12 | None | Integral | Fibres within sample are not swollen or gelled |
| 13 | None | Integral | Fibres within sample are not swollen or gelled |
| 14 | None | Integral | Fibres within sample are not swollen or gelled |
| 15 | None | Integral | Fibres within sample are not swollen or gelled |
| 16 | None | Integral | Fibres within sample are not swollen or gelled |
| 17 | None | Integral | Fibres within sample are not swollen or gelled |

Samples According to the Invention
Sample 18
The same 2.4 dtex cellulose staple fibre (with acetic acid) used in Sample 2 was blended 50/50 with the same chitosan fibres used in Sample 6. No further acid was added. The combined fibres were carded and needled to make a nonwoven fabric.
Sample 19
The same 2.4 dtex cellulose staple fibre (with acetic acid) used in Sample 4 was blended 50/50 with the same chitosan fibres used in Sample 6. The combined fibres were carded and needled to make a nonwoven fabric.
Sample 20
The same 2.4 dtex cellulose staple fibre (with acetic acid and lactic acid) used in Sample 5 was blended 50/50 with the same chitosan fibres used in Sample 6. The combined fibres were carded and needled to make a nonwoven fabric.
Sample 21
The same 2.4 dtex cellulose staple fibre (with acetic acid and lactic acid) used in Sample 5 was blended 50/50 with the same chitosan fibres used in Sample 7. The combined fibres were carded and needled to make a nonwoven fabric.
Sample 22
The same 2.4 dtex cellulose staple fibre (with acetic acid) used in Sample 3 was blended 50/50 with the same chitosan fibres used in Sample 6. The combined fibres were carded and needled to make a nonwoven fabric.
Sample 23
The same 2.4 dtex cellulose staple fibre (with acetic acid and lactic acid) used in Sample 5 was blended 50/50 with the same chitosan fibres used in Sample 7. The combined fibres were carded and flattened to a web/net.
Sample 24
The same 2.4 dtex cellulose staple fibre (with acetic acid and lactic acid) used in Sample 5, and the 2.4 dtex cellulose fibres (no acid) and the chitosan fibres used in Sample 7 were blended 25/25/50. The combined fibres were carded and needled to make a nonwoven fabric.
Sample 25
The same 2.4 dtex cellulose staple fibre (with acetic acid and lactic acid) used in Sample 5, and a 2.4 dtex polypropylene fibre (no acid) and the chitosan fibres used in Sample 7 were blended 25/25/50. The combined fibres were carded and thermally bonded to make a nonwoven fabric.
Sample 26
The same 2.4 dtex cellulose staple fibre (with acetic acid and lactic acid) used in Sample 5, and the chitosan fibres used in Sample 14 were blended 50/50. The combined fibres were carded and needled to make a nonwoven fabric.
Sample 27
The same 2.4 dtex cellulose staple fibre (with acetic acid and lactic acid) used in Sample 5, and the chitosan fibres used in Sample 15 were blended 50/50. The combined fibres were carded and needled to make a nonwoven fabric.
Sample 28
The same 2.4 dtex cellulose staple fibre (with acetic acid and lactic acid) used in Sample 5, and the chitosan fibres used in Sample 16 were blended 50/50. The combined fibres were carded and needled to make a nonwoven fabric.

| Sample | Gelling | Wet Integrity | Comments |
| --- | --- | --- | --- |
| 18 | Good gel | Integral | Fibres within sample are swollen & gelled. Little excess saline is between fibres, most is absorbed within the fibres. Some sliminess suggesting some dissolution. |
| 19 | Some gelling | Integral | Fibres within sample are swollen & gelled. Some excess saline is between fibres, most is absorbed within the fibres. |
| 20 | Good gel | Integral | Fibres within sample are swollen & gelled. Little excess saline is between fibres, most is absorbed within the fibres. |
| 21 | Good gel | Integral | Fibres within sample are swollen & gelled. Little excess saline is between fibres, most is absorbed within the fibres. |

-continued

| Sample | Gelling | Wet Integrity | Comments |
|---|---|---|---|
| 22 | Good gelling but partly dissolving | Integral, some dissolving | Fibres within sample are swollen & gelled. No excess saline is between fibres. Some of the chitosan has dissolved and has produced a viscous liquid which can be squeezed from the fabric. |
| 23 | Good gel | Integral | Fibres within sample are swollen & gelled. Little excess saline is between fibres, most is absorbed within the fibres. |
| 24 | Some good gelling | Integral | Fibres within sample show some gelling/swelling. There is still some saline held between the fibres rather than within them. |
| 25 | Some good gelling | Very integral | Fibres within sample show some gelling/swelling. There is still some saline held between the fibres rather than within them. |
| 26 | Good gel | Integral | Fibres within sample are swollen & gelled. Little excess saline is between fibres, most is absorbed within the fibres. The sample is slightly grey brown. |
| 27 | Good gel | Integral | Fibres within sample are swollen & gelled. Little excess saline is between fibres, most is absorbed within the fibres. The sample showed rapid wet out. |
| 28 | Some good gel | Integral | Fibres within sample are swollen & gelled. A little saline is between fibres, most is absorbed within the fibres. |

It can therefore be seen that the wound care devices according to the invention in Examples 18-28 gel significantly more easily than the single component devices in Samples 1-17.

It is of course to be understood that the present invention is not intended to be restricted to the foregoing examples which are described by way of example only.

The invention claimed is:

1. A fibrous, haemostatic wound dressing comprising:
a first material in a dry fibrous form, said first material comprising chitosan or partially de-acetylated chitin, wherein said first material is not pre-treated with an acid and, by itself, does not gel when exposed to a fluid;
a second material in a dry fibrous form, said second material being selected from the group consisting of: cellulose, a cellulose derivative, cotton, alginate, viscose, polypropylene, polyethylene, and combinations thereof, wherein said second material, by itself, does not gel when exposed to a fluid; and
an acid absorbed in the second material without being permanently bonded to the second material, wherein the acid is selected from the group consisting of: formic acid, acetic acid, ascorbic acid, hydrochloric acid, sulphuric acid, halogen acetic acid, propanoic acid, propenoic acid, lactic acid, succinic acid, acrylic acid, glyoxylic acid, pyruvic acid, 2ydroxyl propionic acid and 2ydroxyl butanoic acid,
wherein said first and second materials are present in the wound dressing in layers or are mixed,
wherein when the haemostatic wound dressing is exposed to a fluid, the acid absorbed in the second material is released from the second material and comes into contact with the first material, said first material chemically reacting with said released acid to form a corresponding salt,
said reaction converting said first material from a non-gelling material into a gellable material whereby said wound dressing can absorb said fluid.

2. A fibrous, haemostatic wound dressing comprising:
a first material comprising chitosan or partially de-acetylated chitin in a dry fibrous form that is not pre-treated with an acid and, by itself, does not gel when exposed to a fluid;
a second material in a dry fibrous form that, by itself, does not gel when exposed to a fluid; and
an acid absorbed in the second material without being permanently bonded to the second material,
wherein when the haemostatic wound dressing is exposed to a fluid, the acid absorbed in the second material is released from the second material and comes into contact with the first material, said first material chemically reacting with said released acid to form a corresponding salt,
said reaction converting said first material from a non-gelling material into a gellable material whereby said wound dressing can absorb said fluid.

3. A wound care device according to claim 2, wherein the second material is selected from the group consisting of: cellulose, a cellulose derivative, cotton, alginate, viscose, polypropylene, polyethylene, and combinations thereof; and wherein the acid is selected from the group consisting of: formic, acetic, ascorbic, hydrochloric, sulphuric, halogen acetic acids, propanoic, propenoic, lactic, succinic, acrylic, glyoxylic, pyruvic, hydroxy propionic and hydroxy butanoic acid.

4. A wound care device according to claim 2, wherein the first and second materials are present in the wound care device in layers, in sections, or are mixed.

5. A wound care device according to claim 2, further comprising one or more therapeutic agents.

6. A wound care device according to claim 2, further comprising at least one of the following: antimicrobial agents, wound healing agents, growth factors, cytokines, and agents which absorb agents which delay healing.

7. A wound care device according to claim 6, wherein the one or more antimicrobial agents is selected from the group consisting of: silver, silver salts, silver-containing compounds, fibres containing silver, and chlorhexidine.

* * * * *